United States Patent
Seeley

(10) Patent No.: US 9,522,281 B2
(45) Date of Patent: *Dec. 20, 2016

(54) VARYING LEAD CONFIGURATION IMPLANTABLE MEDICAL DEVICE

(75) Inventor: Dale F. Seeley, Spring Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 809 days.

This patent is subject to a terminal disclaimer.

(21) Appl. No.: 13/298,386

(22) Filed: Nov. 17, 2011

(65) Prior Publication Data

US 2012/0130437 A1     May 24, 2012

Related U.S. Application Data

(60) Provisional application No. 61/415,069, filed on Nov. 18, 2010.

(51) Int. Cl.
    *A61N 1/00*     (2006.01)
    *A61N 1/375*    (2006.01)
    *H01R 24/00*    (2011.01)

(52) U.S. Cl.
    CPC .......... *A61N 1/3752* (2013.01); *A61N 1/3754* (2013.01); *H01R 24/00* (2013.01); *Y10T 29/49169* (2015.01)

(58) Field of Classification Search
    CPC .... A61N 1/372; A61N 1/37211; A61N 1/375; A61N 1/3752; A61N 1/3754
    USPC .......................... 607/119, 122, 116; 600/528
    See application file for complete search history.

(56) References Cited

U.S. PATENT DOCUMENTS

| 5,383,913 A | 1/1995 | Schiff |
| 5,679,026 A | 10/1997 | Fain |
| 5,899,930 A | 5/1999 | Flynn |
| 6,321,126 B1 | 11/2001 | Kuzma |

(Continued)

FOREIGN PATENT DOCUMENTS

| EP | 2 153 868 A1 | 2/2010 |
| WO | WO 2008/025159 A1 | 3/2008 |

(Continued)

OTHER PUBLICATIONS

PCT/US2011/061114; Search Report and Written Opinion dated May 3, 2012.

(Continued)

*Primary Examiner* — Edward Moran
*Assistant Examiner* — Elizabeth K So
(74) *Attorney, Agent, or Firm* — Mueting, Raasch & Gebhardt, P.A.

(57) ABSTRACT

An implantable electrical medical device includes (i) electronics configured to generate or receive an electrical signal and containing a plurality of channels through which the electrical signal may be transmitted; (ii) a first lead receptacle having a first defined number of internal contacts, wherein each of the internal contacts are independently operably coupled to a discrete channel of the electronics; and (iii) a second lead receptacle having a second defined number of internal contacts, wherein the second defined number is less than the first defined number, and wherein each of the internal contacts of the second receptacle are independently operably coupled to a discrete channel of the electronics. At least one of the internal contacts of the first lead receptacle and at least one of the internal contacts of the second lead receptacle are operably coupled to the same channel of the electronics.

20 Claims, 9 Drawing Sheets

(56) References Cited

U.S. PATENT DOCUMENTS

| | | |
|---|---|---|
| 7,031,774 B1 | 4/2006 | Doan |
| 7,083,474 B1 | 8/2006 | Fleck |
| 7,376,465 B2 | 5/2008 | Hornfeldt |
| 7,515,964 B1 | 4/2009 | Alexander |
| 7,537,474 B2 | 5/2009 | Deininger et al. |
| 7,563,141 B2 | 7/2009 | Alexander |
| 7,702,385 B2 | 4/2010 | Moffitt |
| 7,856,272 B2 | 12/2010 | Nikitin |
| 2003/0171783 A1 | 9/2003 | Tsukamoto et al. |
| 2004/0106964 A1 | 6/2004 | Fischer, Sr. et al. |
| 2006/0167522 A1 | 7/2006 | Malinowski |
| 2006/0224208 A1 | 10/2006 | Naviaux |
| 2007/0111587 A1 | 5/2007 | Ries et al. |
| 2008/0015668 A1 | 1/2008 | Soukup |
| 2009/0018601 A1 | 1/2009 | Deininger et al. |
| 2010/0137929 A1 | 6/2010 | Libbey |
| 2010/0274309 A1 | 10/2010 | Knipfer et al. |
| 2010/0331924 A1* | 12/2010 | North ................... A61N 1/3754 607/72 |
| 2011/0004279 A1* | 1/2011 | North ................... A61N 1/3752 607/72 |
| 2012/0083867 A1* | 4/2012 | Wahlstrand et al. ......... 607/116 |

FOREIGN PATENT DOCUMENTS

| | | |
|---|---|---|
| WO | WO 2010/148379 | 12/2010 |
| WO | WO 2011/002913 A1 | 1/2011 |
| WO | WO 2012/027126 A1 | 3/2012 |
| WO | WO 2012/068385 A1 | 5/2012 |

OTHER PUBLICATIONS

PCT/US2011/061114; International Preliminary Examination Report dated May 21, 2013.
PCT/US2011/061208, International Preliminary Report on Patentability, dated May 30, 2013, 11 pages.
PCT/US2011/061208, International Search Report and Written Opinion, dated Sep. 12, 2012, 17 pages.
PCT/US2011/061208, Invitation to Pay Additional Fees with Partial Search Report, dated May 3, 2012, 8 pages.

\* cited by examiner

VARYING LEAD CONFIGURATION IMPLANTABLE MEDICAL DEVICE

RELATED APPLICATION

This application claims the benefit of priority to U.S. Provisional Application No. 61/415,069, filed on Nov. 18, 2010, which application is hereby incorporated by reference in its entirety to the extent that it does not conflict with the disclosure presented herein.

FIELD

This application relates to implantable medical devices; more particularly to systems and devices that include an implantable electrical medical device, such as an electrical signal generating device or monitoring device.

BACKGROUND

Implantable electrical signal generators have been used to treat a variety of diseases and have been used in a variety of manners. For example, deep brain stimulation has been used to treat Parkinson's disease and essential tremor, and spinal cord stimulation or peripheral nerve stimulation has been used to treat pain. Implantable medical leads are operably coupled to the signal generators and carry electrical signals to appropriate locations of the patient so that a therapeutic benefit may be obtained.

A variety of different implantable leads may be selected for use in such therapies. However, currently available implantable signal generators are configured to be coupled to leads of a given type. For example, an implantable electrical signal generator may be configured to receive one or two eight electrode leads. To use four electrode leads with such a device, an adaptor or bifurcating lead extension may be employed.

In the past electrical signal generators, such as neurostimulators, were generally limited to 8 or 16 channels (e.g., capable of providing independent electrical signals to only eight or 16 electrodes). However, with technological advancement, implantable signal generators may have significantly more channels, such as 32 or 64, which allows for more electrodes to be used in therapy. Yet, such signal generators are still configured to accept only particular types of leads, unless an adaptor or the like is used.

BRIEF SUMMARY

The present disclosure describes, among other things, implantable electrical medical devices, such as signal generators, and systems that may be simultaneously operably coupled to a variety of types of leads, such as four electrode leads and eight electrode leads. Accordingly, a physician may readily employ more than one type of lead with a single implantable signal generator. This may provide the physician with the ability to employ more flexible treatment strategies for a particular disease or to provide a variety of therapies, such as spinal cord stimulation and subcutaneous stimulation, at the same time. In addition or alternatively, the physician may no longer need to select from a variety of makes and models of implantable electrical medical devices depending on the therapeutic needs of the patient, but rather may use a single device in a variety of situations.

In embodiments, an implantable electrical medical device includes (i) electronics configured to generate or receive an electrical signal, the electronics containing a plurality of channels through which the electrical signal may be transmitted; (ii) a first lead receptacle having a defined number of internal contacts, wherein each of the internal contacts are independently operably coupled to a discrete channel of the electronics; and (iii) a second lead receptacle having a defined number of internal contacts, wherein the defined number of internal contacts of the second lead receptacle is less than the defined number of internal contacts of the first receptacle, and wherein each of the internal contacts of the second receptacle are independently operably coupled to a discrete channel of the electronics. At least one of the internal contacts of the first lead receptacle and at least one of the internal contacts of the second lead receptacle are operably coupled to the same channel of the electronics. By way of example and in some embodiments, a first internal contact of the first lead receptacle is operably coupled to a first channel of the electronics, wherein a second internal contact of the first lead receptacle is operably coupled to a second channel of the electronics, wherein a first internal contact of the second lead receptacle is operably coupled to the first channel of the electronics, and wherein a second internal contact of the second lead receptacle is operably coupled to the second channel of the electronics. In some embodiments, the device may further include a third lead receptacle having a defined number of internal contacts, wherein the defined number of internal contacts of the second lead receptacle is less than the defined number of internal contacts of the first receptacle, wherein the defined number of internal contacts of the second lead receptacle is the same or different than the defined number of internal contacts of the second receptacle, and wherein each of the internal contacts of the third receptacle are independently operably coupled to a discrete channel of the electronics. At least one of the internal contacts of the first lead receptacle and at least one of the internal contacts of the third lead receptacle are operably coupled to the same channel of the electronics. It will be understood that the device may include more than three receptacles in some embodiments. It will also be understood that the device may have any number of channels, such as 8, 16, 32, or 64 channels, which may be electrically coupled to the internal contacts of the various receptacles, e.g., as described in more detail below.

In embodiments, a method for manufacturing an implantable medical device having redundant connections between contacts of one or more lead receptacles and channels of electronics includes (i) providing a device body having a hermetically sealed housing, electronics disposed in the housing, and a plurality of feedthroughs extending through the hermetically sealed housing, wherein each of the plurality of feedthroughs is electrically coupled to a discrete channel of the electronics; (ii) providing a header having first and second lead receptacles into which leads may be inserted, the first and second lead receptacle each having a defined number of internal contacts wherein the defined number of internal contacts of the second lead receptacle is less than the defined number of internal contacts of the first lead receptacle; (iii) electrically coupling each of the contacts of the first lead receptacle to a discrete channel of the electronics; and (iv) electrically coupling each of the contacts of the second lead receptacle to a discrete channel of the electronics. At least one of the internal contacts of the first lead receptacle and at least one of the internal contacts of the second lead receptacle are operably coupled to the same channel of the electronics In embodiments, an implantable electrical medical device includes (i) electronics configured to generate or receive an electrical signal, the electronics containing a plurality of channels through which the electrical signal may be transmitted; (ii) a first lead receptacle having a defined number of internal contacts, wherein each of the internal contacts is independently operably coupled to a discrete channel of the electronics; (iii) a second lead receptacle having a defined number of internal contacts, wherein each of the internal contacts is independently operably coupled to a discrete channel of the electronic; and (iv) a third lead receptacle having a defined number of internal contacts, wherein each of the internal contacts is independently operably coupled to a discrete channel of the electronics. A first set of one or more of the internal contacts of the first lead receptacle and a set of one or more of the internal contacts of the second lead receptacle are independently operably coupled to the same first set of one or more channels of the electronics. A second set of one or more of the internal contacts of the first lead receptacle and a set of one or more of the internal contacts of the third lead receptacle are independently operably coupled to the same second set of one or more channels of the electronics. Each of the contacts of the first set of internal contacts of the first lead receptacle is different from each of the contacts of the second set of internal contacts of the first lead receptacle.

In embodiments, a method for manufacturing an implantable medical device having redundant connections between contacts of one or more lead receptacles and channels of electronics includes (i) providing a device body having a hermetically sealed housing, electronics disposed in the housing, and a plurality of feedthroughs extending through the hermetically sealed housing, wherein each of the plurality of feedthroughs is electrically coupled to a discrete channel of the electronics; (ii) providing a header having first, second and third lead receptacles into which leads may be inserted, the first and second lead receptacle each having a defined number of internal contacts wherein the defined number of internal contacts of the second lead receptacle is less than the defined number of internal contacts of the first lead receptacle; (iii) electrically coupling each of the contacts of the first lead receptacle to a discrete channel of the electronics; (iv) electrically coupling each of the contacts of the second lead receptacle to a discrete channel of the electronics; and (v) electrically coupling each of the contacts of the third lead receptacle to a discrete channel of the electronics. A first set of one or more of the internal contacts of the first lead receptacle and a set of one or more of the internal contacts of the second lead receptacle are independently operably coupled to the same first set of one or more channels of the electronics. A second set of one or more of the internal contacts of the first lead receptacle and a set of one or more of the internal contacts of the third lead receptacle are independently operably coupled to the same second set of one or more channels of the electronics. Each of the contacts of the first set of internal contacts of the first lead receptacle is different from each of the contacts of the second set of internal contacts of the first lead receptacle In embodiments, an implantable electrical medical device includes (i) electronics configured to generate or receive an electrical signal, the electronics containing a plurality of channels through which the electrical signal may be transmitted; (ii) a first lead receptacle having a defined number of internal contacts, wherein each of the internal contacts are independently operably coupled to a discrete channel of the electronics; and (iii) a second lead receptacle the same number of internal contacts as the first lead receptacle, and wherein each of the internal contacts of the second receptacle are independently operably coupled to a discrete channel of the electronics. Each channel of the electronics to which a contact of the first receptacle is operably coupled is also operably coupled to a channel of the second receptacle. The first and second lead receptacle are configured to receive leads having contacts with different spacing.

In embodiments, a method for manufacturing an implantable medical device having redundant connections between contacts of one or more lead receptacles and channels of electronics includes (i) providing a device body having a hermetically sealed housing, electronics disposed in the housing, and a plurality of feedthroughs extending through the hermetically sealed housing, wherein each of the plurality of feedthroughs is electrically coupled to a discrete channel of the electronics; (ii) providing a header having first and second lead receptacles into which leads may be inserted, the first and second lead receptacle each having a defined number of internal contacts wherein the defined number of internal contacts of the second lead receptacle is less than the defined number of internal contacts of the first lead receptacle; (iii) electrically coupling each of the contacts of the first lead receptacle to a discrete channel of the electronics; and (iv) electrically coupling each of the contacts of the second lead receptacle to a discrete channel of the electronics. Each channel of the electronics to which a contact of the first receptacle is operably coupled is also operably coupled to a channel of the second receptacle. The first and second lead receptacle may be configured to receive leads having contacts with different spacing.

One or more embodiments of the devices, systems or methods described herein may provide one or more advantages over existing systems, devices and methods. One of skill in the art will appreciate the advantages provided upon reading the description that follows.

Figure 1:
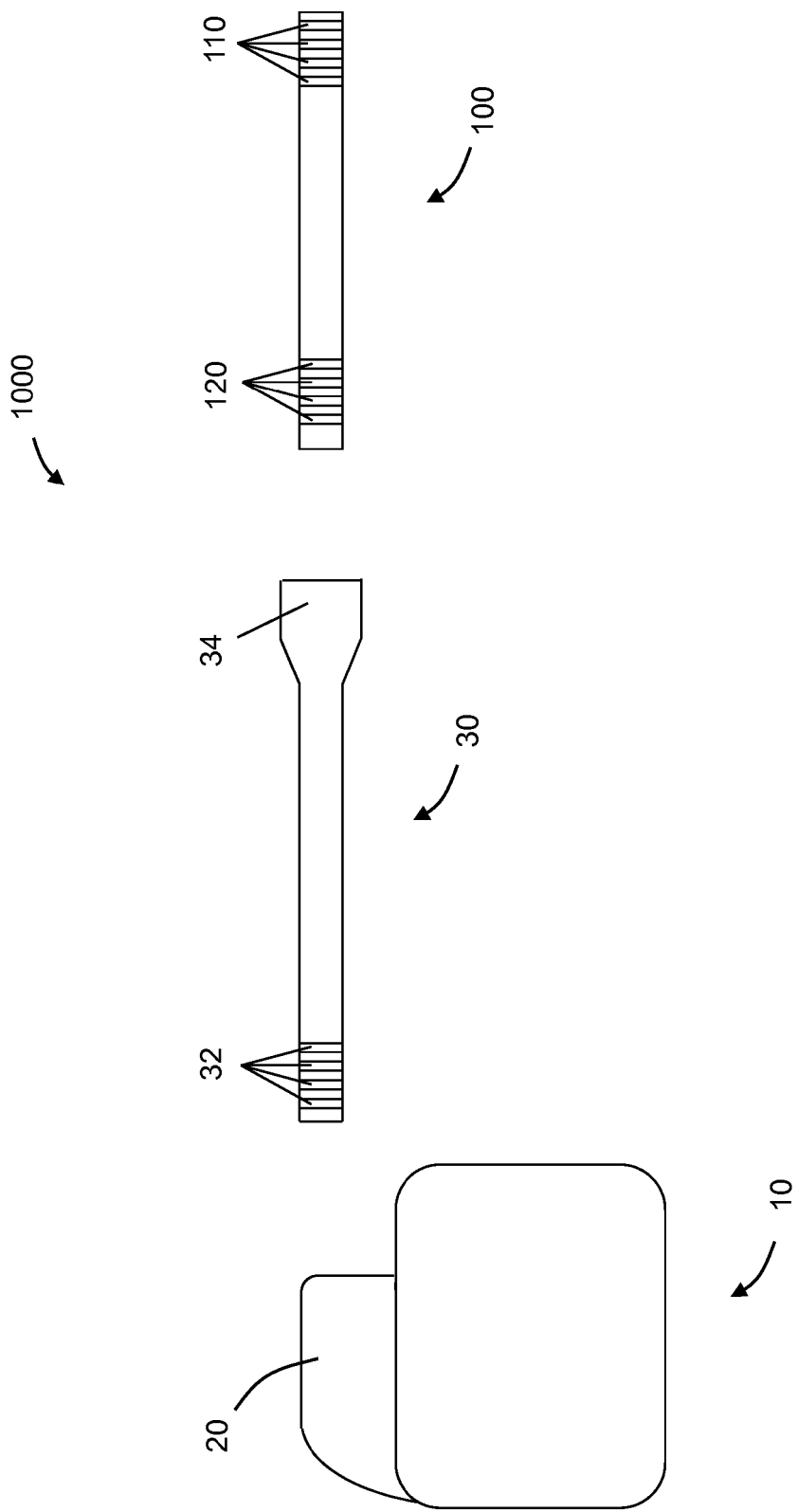
FIG. 1 is a schematic side view of an implantable system including an implantable electrical medical device, a lead extension and a lead.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not necessarily intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising."

Any direction referred to herein, such as "top," "bottom," "left," "right," "upper," "lower," "above," below," and other directions and orientations are described herein for clarity in reference to the figures and are not to be limiting of an actual device or system or use of the device or system. Devices or systems as described herein may be used in a number of directions and orientations.

As used herein, "independently operably coupled," in the context of a set of contacts to a set of channels of electronics, means that each contact of the set of contacts is operably coupled to a discrete channel of the set of channels of the electronics. For example, if a set of three contacts consists of contact A, contact B and contact C, and a set of three channels consists of channel 1, channel 2, and channel 3, the set of contacts would be independently operably coupled to the set of channels if, for example, contact A were discretely operably coupled to channel 1, contact B were discretely operably coupled to channel 2, and contact C were discretely operably coupled to channel 3. Further, if a first set of contacts and a second set of contacts are independently operably coupled to the same set of channels, then each contact of the first set of contacts is operably coupled to a discrete channel of the set of channels of the electronics and each contact of the second set of contacts is operably coupled to an independent channel of the set of channels, to which independent channel a contact from the first set of contacts is also operably coupled.

As used herein, a "channel of the electronics" of an implantable electrical medical device means a discrete electronic pathway through which data or electrical signals may be transmitted. For example, an electrical signal generator may include an oscillator independently operably coupled to multiple channels so that differing electrical signals (e.g., voltage or current) may be transmitted from the electronics to multiple electrodes of leads, each of which is independently operably coupled to a channel of the electronics.

The present disclosure, among other things relates to, among other things, electrical medical devices, such as electrical signal generators or monitoring devices, and systems that may employ multiple medical leads. The systems and devices described herein may provide for flexibility in the number and types of leads that may be operably coupled to an implantable electrical medical device. The leads may be signal emitting leads or sensing leads.

Nearly any implantable medical device or system employing leads may be used in conjunction with the leads, extensions or adaptors described herein. Representative examples of such implantable medical devices include hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like.

Referring to FIG. 1, a side view of a schematic implantable system 1000 is shown. In the depicted system 1000, the implantable electrical medical device 10 includes a connector header 20 configured to receive a proximal portion of lead extension 30. The proximal portion of lead extension 30 contains a plurality of electrical contacts 32 that are electrically coupled to internal contacts (not shown) at distal connector 34 of lead extension 30. The connector header 20 of the signal generator 10 contains internal contacts (not shown) and is configured to receive the proximal portion of the lead extension 30 such that the internal contacts of the connector header 20 may be electrically coupled to the contacts 32 of the lead extension 30 when the lead extension 30 is inserted into the header 20.

The system depicted in FIG. 1 further includes a lead 100. The depicted lead 100 has a proximal portion that includes a plurality of contacts 120 and a distal portion that includes a plurality of electrodes 110. Each of the electrodes 110 may be electrically coupled to a discrete contact 120. The distal connector 34 of the lead extension 30 is configured to receive the proximal portion of the lead 100 such that the contacts 120 of the lead 100 may be electrically coupled to the internal contacts of the connector 34 of the extension 30. Accordingly, a signal generated by the implantable electrical device 10 may be transmitted to a tissue of a patient by an electrode 110 of lead 100 when lead is connected to extension 30 and extension 30 is connected to implantable electrical device 10. Alternatively or in addition, a signal received by electrode 110 of lead 100 from a patient may be transmitted to a contact of the device 10 when lead is connected to extension 30 and extension 30 is connected to the device 10.

It will be understood that lead 100 may be coupled to implantable medical device 10 without use of an extension 30. Any number of leads 100 or extensions 20 may be coupled to device 10. While lead 100 is depicted as having four electrodes 110, it will be understood that lead 100 may include any number of electrodes 110, e.g. one, two, three, four, five, six, seven, eight, sixteen, thirty-two, or sixty-four. Corresponding changes in the number of contacts 120 in lead 100, contacts 32 and internal contacts in connector 34 of lead extension, or internal contacts in connector 20 of device 10 may be required or desired.

As used hereinafter, "lead" will refer to both "leads" and "lead extensions" unless the content and context clearly dictates otherwise.

Figure 2A:
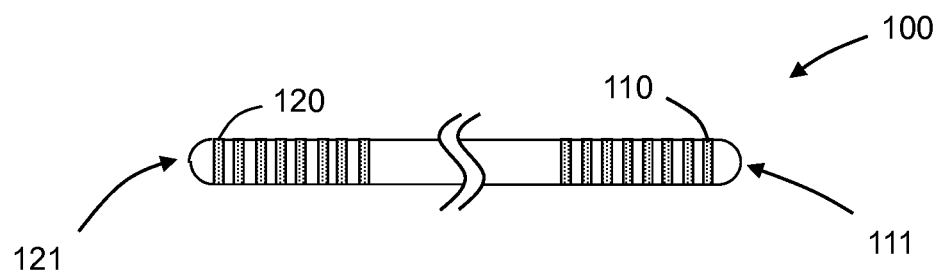
FIGS. 2A-B are schematic side views of an implantable medical leads.
Figure 2B:
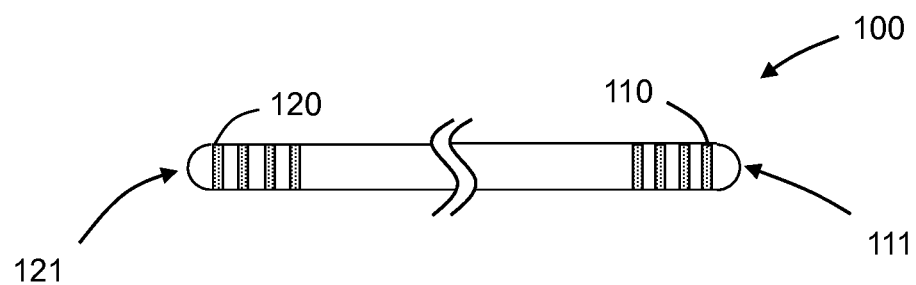

Referring now to FIGS. 2A-B, schematic side views of leads 100 are shown. The leads 100 have a proximal end 121 and a distal end 111. A plurality of contacts 120 are disposed in proximity to the proximal end 121 of the lead 100, and a plurality of electrodes 110 are disposed in proximity to the distal end 111 of the lead 100. Typically, each contact 120 is electrically coupled to a discrete electrode 110, such as through an insulated conductive wire running within the body of the lead. The proximal end 121 of the lead is insertable into a receptacle of an implantable electrical medical device such that the contacts 120 of the lead 100 may be electrically coupled with internal contacts of the receptacle.

The lead depicted in FIG. 2A has eight contacts 120 and eight electrodes 110, while the lead depicted in FIG. 2B has four contacts 120 and four electrodes 110. The pitch, i.e. space between contacts 120, is different between the four (2B) and eight (2A) electrode leads, which is typical of such leads. In the depicted eight electrode 110 lead (2A) the contacts 120 are closer to each other than in the depicted four electrode 110 lead (2B).

Figure 3A:
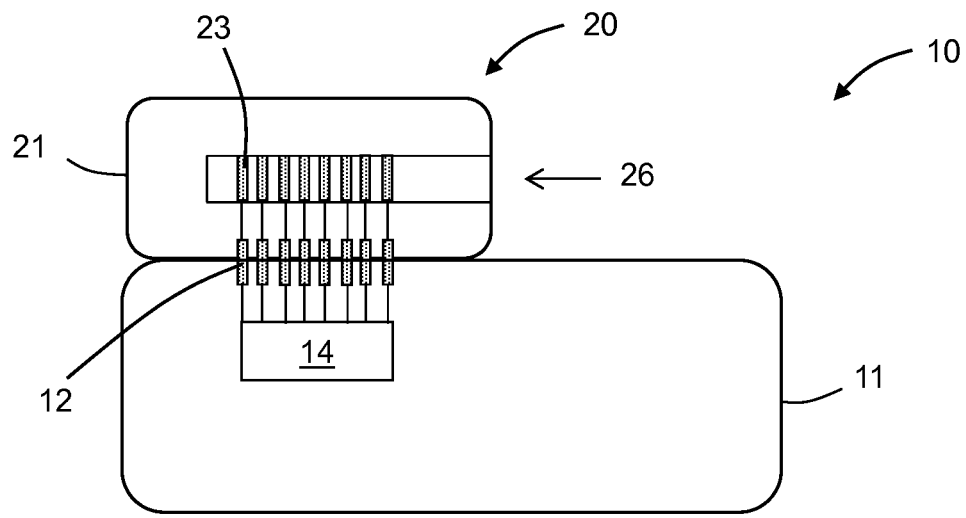
FIGS. 3A-3B are schematic side views of implantable electrical devices, showing some internal components.
Figure 3B:
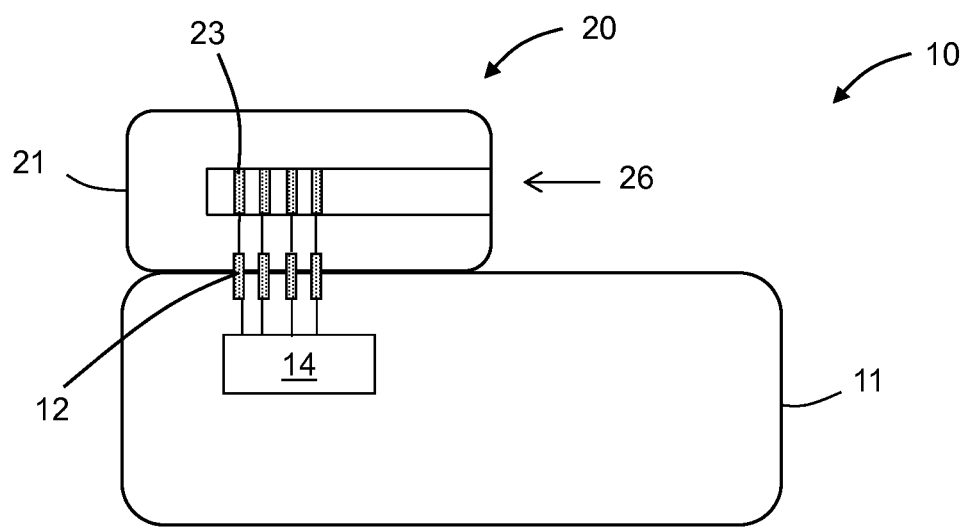

Referring now to FIGS. 3A-B, schematic sectional side views of implantable electrical medical devices 10 are shown. The devices 10 depicted in FIGS. 3A and 3B, respectively, are configured to receive and operably couple to the leads 100 depicted in FIGS. 2A and 2B, respectively. The devices 10 depicted in FIGS. 3A-B include a hermetically sealed housing 11 in which electronics 14 are disposed, and a connector header 20 disposed on the device housing 11. A lead receptacle 26 is formed in the housing 21 of the header 20. The receptacle 26 is configured to receive and electrically couple to contacts of a lead.

The receptacle has internal contacts 23 positioned to align with and electrically couple with contacts of a lead when the lead is properly inserted into the receptacle. The pitch, or spacing of, internal contacts 23 of the receptacle 26 depicted in FIG. 3A is different from the pitch of the internal contacts 23 depicted in FIG. 3B. The pitch of the internal contacts 23 of FIG. 3A is configured to allow electrical connection between the contacts 121 of a lead as depicted in FIG. 2A. The pitch of the internal contacts 23 of FIG. 3B is configured to allow electrical connection between the contacts 121 of a lead as depicted in FIG. 2B. Implantable electrical devices, according to embodiments described herein in more detail below, may have headers with multiple lead receptacles with different receptacles configured to be coupled to different leads, such as leads having four, eight or sixteen electrodes.

Still referring to FIGS. 3A-B, electronics 14 are configured to send electrical signals to tissue of a patient, or receive signals from a tissue of a patient, through the leads. As depicted, channels of the electronics are discretely coupled to internal contacts 23 of lead receptacles 26 via feedthroughs 12, which extend through hermetically sealed housing 11. The feedthroughs 12 may be electrically coupled with internal contacts 23 via welding soldering, coupling via conductive wires, or the like. Each channel of the electronics 14 can be independently coupled with a discrete internal contact 23 of a receptacle, which can be coupled with a discrete contact of a lead, which can be coupled with a discrete electrode of the lead. Accordingly, each channel of the electronics 14 may be operably coupled to a given electrode of a lead.

One problem with existing implantable electrical devices is that they are generally configured to receive only one type of lead, e.g., a four electrode (quad) lead or an eight electrode (Octad) lead. In embodiments, the devices described herein have multiple receptacles, some of which are configured to receive and operably couple to, for example, an Octad electrode lead and some of some of which are configured to receive and operably couple to, for example, an quad lead.

Figure 4A:
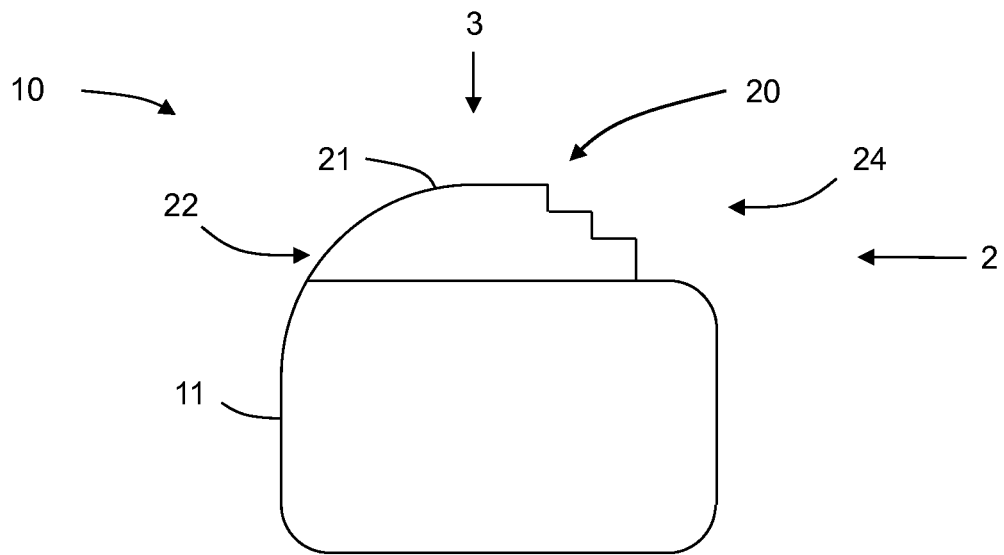
FIG. 4A is a schematic side view of an embodiment of an implantable electrical medical device.
Figure 4B:
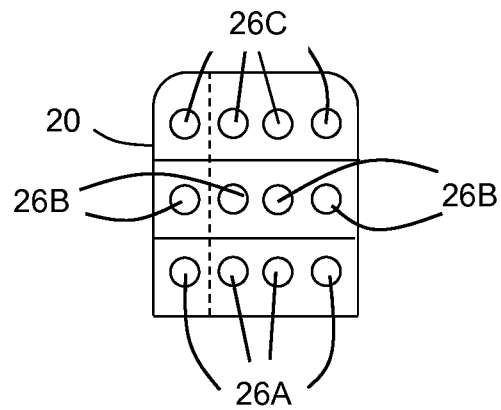
FIGS. 4B-C are schematic front (4B) and top (4C) views of an embodiment of the implantable electrical medical device shown in FIG. 4A.
Figure 4C:
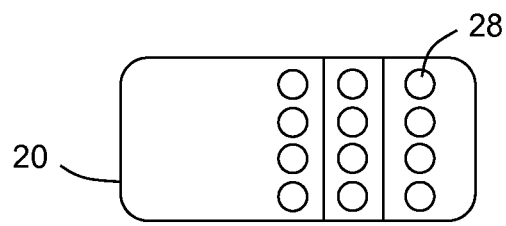

By way of example and with reference to FIGS. 4A-C, schematic side, front, and top views of implantable electrical device 10 or header 20 are shown. The connector header 20 has 12 bores or receptacles with a top row of four receptacles 26C, a middle row of four receptacles 26B, and a bottom row of four receptacles 26A. The front face 24 of the upper row of receptacles 26C is offset towards the back 22 of the header 20 relative to the middle row of receptacles 26B. The front face 24 of the middle row of receptacles 26B is offset towards the back 22 of the header 20 relative to the lower row of receptacles 26A. In this manner, set screws 28 (see FIG. 4C) are accessible from the top of the header 20. Each receptacle 26A, 26B, 26C has a corresponding set screw 28 tightenable relative to the header housing 21 for securing a lead within the respective receptacle. Of course any mechanism other than a set screw for securing a lead within a receptacle may be used.

In the embodiment depicted in FIGS. 4A-B, leads may be first inserted into one or more of the lower receptacles 26A and the appropriate set screws tightened prior to insertion of leads into one or more of the middle receptacles 26B (as insertion of leads into the middle receptacles may interfere with the ability to tighten the set screws of the lower receptacles). Similarly, leads may be first inserted into one or more of the middle receptacles 26B and the appropriate set screws tightened prior to insertion of leads into one or more of the upper receptacles 26C.

The implantable electrical medical device 10 depicted in FIGS. 4A-C may have any suitable number of channels, such as 64 channel or 32 channels. By way of example, the lower row of four receptacles 26A may each have eight internal contacts, while each of the middle 26B and upper 26C receptacles may have four internal contacts. Accordingly, the device 10 may allow for operable connection of a variety of types of leads without the use of adaptors or the like.

If the device 10 depicted in FIGS. 4A-C has 32 channels and the lower receptacles 26A each have eight internal contacts and the middle 26B and upper receptacles 26C each have four internal contacts, then the device 10 would have more than one internal contact per channel. This provides redundant connections of the channels to more than one receptacle that provides a benefit to an implanting physician to be able to choose what lead and connection to make during an implant procedure. Providing redundant connections can be accomplished in any of a number of ways, such as coupling each contact of a middle receptacle 26B to a channel to which a contact of a lower receptacle 26A is coupled and coupling each contact of an upper receptacle 26C to a channel to which a contact of a lower receptacle 26A is coupled. In this way, four internal contacts of a lower receptacle 26A will be coupled to a channel to which a contact of a middle receptacle 26B is coupled, and four other contacts another lower channel 26A will be coupled to a channel to which a contact of an upper receptacle 26C is coupled.

Figure 5:
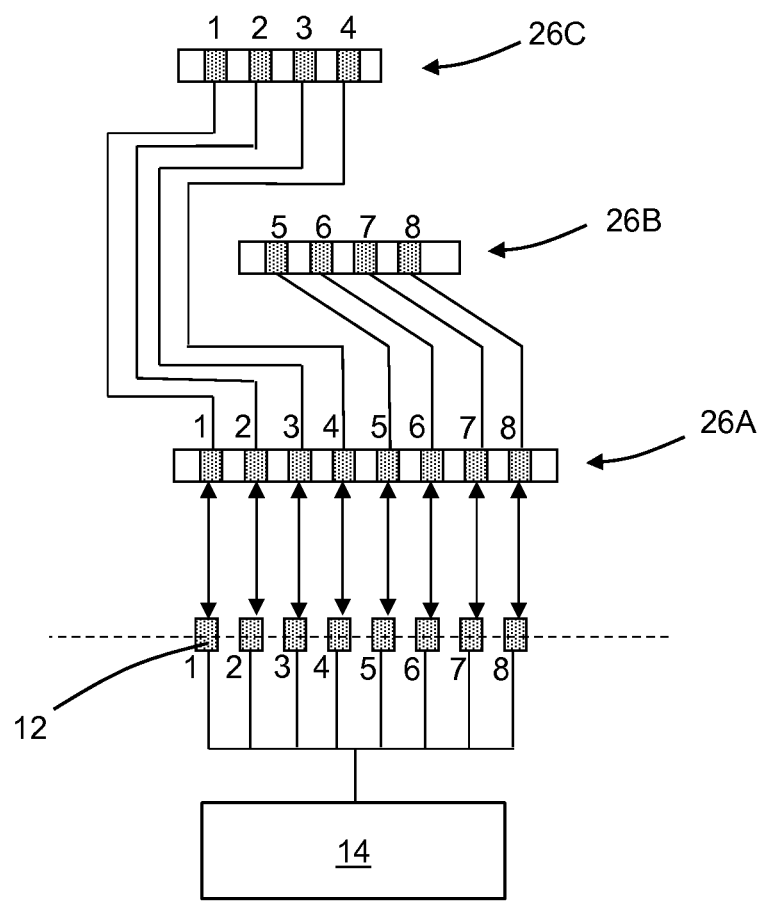
FIG. 5 is a schematic diagram showing electrical connections between contacts of selected receptacles and electronics of an embodiment of the device depicted in FIGS. 4A-C.
Figure 6:
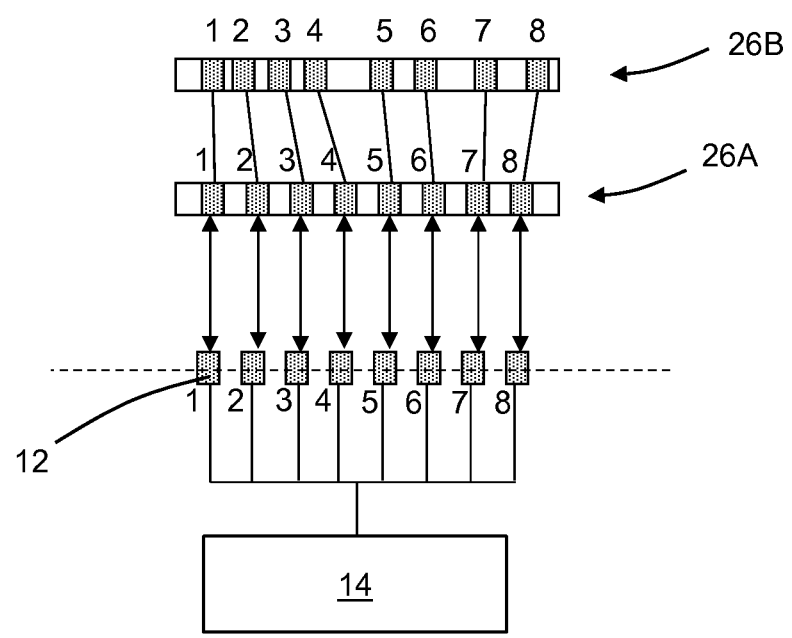
FIG. 6 is a schematic diagram showing an embodiment of electrical connections between contacts of selected receptacles and electronics.

By way of example and with reference to FIGS. 5-6, possible scenarios for redundant contacts in the above-described situation is schematically illustrated. In FIG. 5, the header housing and device housing are not shown for purposes of convenience. However, the dashed horizontal line represents the position of the device housing relative to feedthroughs 12. The receptacles 26A-C shown in FIG. 5 may be, for example, the receptacles to the left of the dashed vertical line depicted in FIG. 4; i.e., a receptacle from the lower group 26A, a receptacle from the middle group 26B, and a receptacle from the upper group 26C.

As shown in FIG. 5, the four contacts of receptacle 26C and four of the eight contacts of receptacle 26A may be coupled to the first four channels of electronics 14, which may include a signal generator. That is, contact 1 of receptacle 26C and contact 1 of receptacle 26A may be coupled to channel 1; contact 2 of receptacle 26C and contact 2 of receptacle 26A may be coupled to channel 2; contact 3 of receptacle 26C and contact 3 of receptacle 26A may be coupled to channel 3; and contact 4 of receptacle 26C and contact 4 of receptacle 26A may be coupled to channel 4.

As shown further shown in FIG. 5, the four contacts of receptacle 26B and four of the eight contacts of receptacle 26A may be coupled to channels 5-8 of the signal generator. That is, contact 5 of receptacle 26B and contact 5 of receptacle 26A may be coupled to channel 5; contact 6 of receptacle 26B and contact 6 of receptacle 26AC may be coupled to channel 6; contact 7 of receptacle 26B and contact 7 of receptacle 26A may be coupled to channel 7; and contact 8 of receptacle 26B and contact 8 of receptacle 26A may be coupled to channel 8.

Thus, a lead having eight contacts (and eight electrodes) may be inserted into receptacle 26A. A lead having four contacts (and four electrodes) may be inserted into either of receptacles 26B or 26C.

Referring now to FIG. 6 a device may have redundant connections between channels of the electronics 14 and contacts of receptacles 26A, 26B where the receptacles have the same number of contacts. In the embodiment depicted in FIG. 6, the contacts (1-8) of receptacle 26A are spaced differently than the contacts (1-8) of receptacle 26B. While both receptacle 26A and receptacle 26B are configured to receive leads with eight contacts, they are not configured to receive the same lead because the spacing of the contacts in the receptacles is different. By way of example, an older model eight electrode lead that has been implanted in a patient for years may have different proximal contact spacing than a newer model eight electrode lead. A device having redundant contacts as depicted in FIG. 6, would be able to be connected to either the older model lead or the newer model lead. Accordingly, if an old device is being replaced but the implanted lead still functions properly, an implanting physician can choose to insert the previously implanted lead into the appropriate receptacle of the new device. Alternatively, if the physician is implanting a new device and a new lead, the physician may select the other receptacle for coupling the new lead.

With reference now to FIG. 4B and FIG. 5, each column of receptacles 26A-C depicted in FIG. 4B may be arranged in a manner similar to that depicted in FIG. 5. That is, within a column, four internal contacts of the lower receptacle 26A may be coupled to a channel of the electronics 14 to which a contact of the middle receptacle 26B is coupled, and four other contacts on the lower channel 26A will be coupled to a channel to which a contact of the upper receptacle 26C is coupled. Accordingly, a physician may choose to use four eight-contact Octad leads with one lead inserted into each of the receptacles 26A of the lower row, eight four-contact quad leads with leads inserted into each of the middle 26B and upper 26C receptacles, or combinations or derivations thereof. For example, two Octad leads may be inserted into the left two lower receptacles 26A, and four quad leads may be inserted into the right two middle 26B and upper 26C receptacles. In this manner, the two Octad leads may be used for, e.g., spinal cord stimulation, and the four quad leads may be used for, e.g., subcutaneous stimulation. Thus, one implantable electrical device may be used for more than one therapy. Alternatively, or in addition, a physician may choose more than one type of lead for use with a given therapy, which was not previously possible without the use of adaptors, or the like. Such flexibility in lead choice, which is possible with the devices described herein, may allow for more tailored therapy for a given patient.

While the discussion above with regard to FIG. 4B and FIG. 5 describes the use of either one Octad lead or two quad leads in any given receptacle column 26A-C, it will be understood that it would be acceptable for some columns of receptacles to have no leads inserted when the device is in use. It should also be understood that both four contact receptacles (26B, 26C) need not have inserted leads when the device is in use. It will be further understood, that a quad lead may be inserted into a four contact receptacle (26B, 26C) while an Octad lead is inserted into an eight contact receptacle 26A within the same column. However, the quad lead and the corresponding four contacts and electrodes of the Octad lead will not be independently controllable by the electronics 14 as they would be coupled to the same channels.

It may be desirable to produce a robust factory seal (not shown) across the opening of receptacle 26A, 26B, 26C having a contact redundantly coupled to a channel of the device. The seal, which may be a silicone plug, must be broken or removed prior to inserting a lead into the receptacle. The remaining seals or plugs will ensure that current or voltage leakage, as well as concomitant "pocket stimulation," will be minimized.

Figure 7:
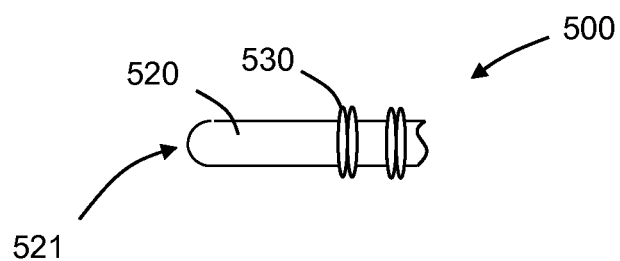
FIG. 7 is a schematic side view of a portion of a plug.

One example of a plug 500 that may be inserted into an unused receptacle is depicted in FIG. 7. The plug 500 is electrically inert and has a body 520 having a proximal end 521, which may be inserted into a receptacle. One or more seals 530 may be disposed about the body to prevent leakage of current or voltage and to prevent invasion of body fluids when implanted. Preferably, the proximal end of the plug body 520 extends a sufficient distance from the face of the connector header forming the bore of the receptacle that the plug 500 may be readily grasped, e.g. with a tool, and removed from the receptacle so that a lead may be inserted into the receptacle, if desired. In embodiments, the plug 500 is constructed in a manner similar to a lead, without contacts, electrodes, conductors, etc.

Figure 8:
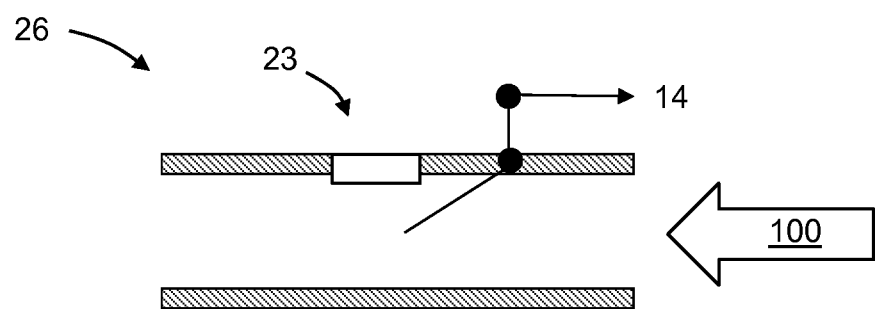
FIG. 8 is a schematic diagram showing a switch operably coupled to a contact of a lead receptacle.

Alternatively, or in addition, and with reference to FIG. 8, the internal contacts 23 of the receptacles 26 may be operably coupled to or part of switches biased in the off position. Insertion of a lead 100 into the receptacle 26 causes the circuit to close and switches the contact 23 on so that signals may be sent to or from the contact 23 from or to the electronics 14. It will be understood, that any suitable switch may be employed. One switch may be employed for all of the contacts in a receptacle or each contact of the receptacle may have an independent switch.

In embodiments, electronics of the implantable electrical medical device are configured to check impedance of the internal contacts of the receptacles to determine whether a lead is inserted or properly inserted into the lead receptacle. The receptacles or electronics may be configured to selectively activate only those receptacles in which leads are properly inserted. Examples of impedance circuits and methods that may be employed include those described in, for example, U.S. Pat. Nos. 5,201,865 and 5,897,577.

Referring again to FIGS. 4A-B, as can be imagined, it may be difficult to manage four or more leads extending from one device 10, where all the leads extend from one face 24 of a single header 20. For example, it may be difficult to wrap all of the leads around the device 10 and neatly tuck them into a subcutaneous implant pocket in a patient.

Figure 9:
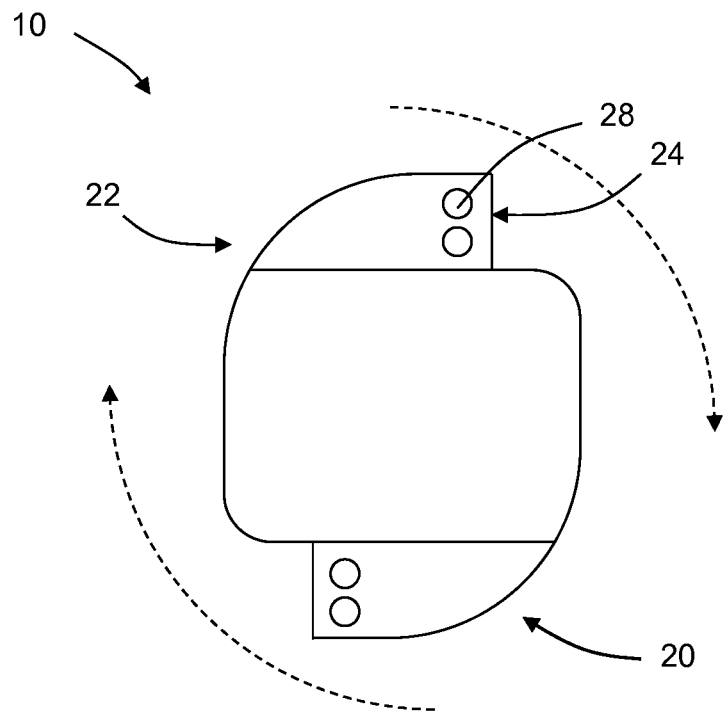
FIGS. 9-10 are schematic side views of implantable electrical medical devices having two connector headers.
Figure 10:
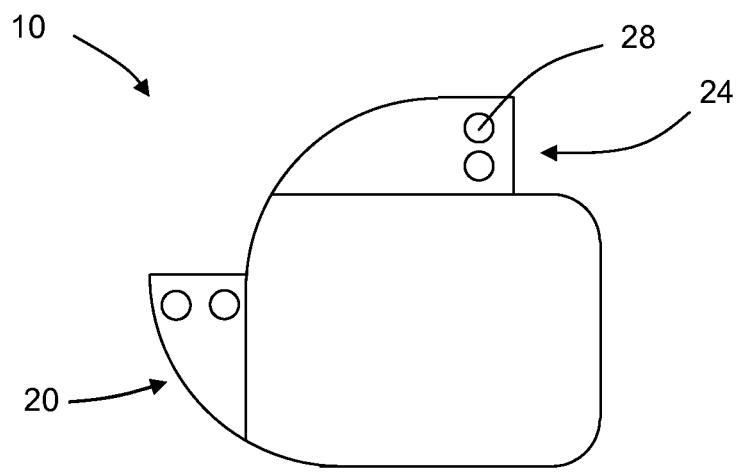

Referring now to FIGS. 9-10, embodiments of implantable electrical medical devices 10 having more than one connector header 20 are shown. The connector headers 20 are arranged such that the orientation from back 22 to front 24 of each of the headers 20 is clockwise around the device 10. Of course, each of the headers 20 could be oriented in a counter-clockwise manner around the housing. By orienting the headers 20 in this manner, the leads that extend from the headers may be easily wrapped around the device 10 in the same direction, without all of the leads extending from a single header. While only two headers are shown in FIGS. 9-10, it will be understood that any number of three or four or more headers may be arranged around the housing in a similar manner.

Still referring to FIGS. 9-10, the depicted headers 20 are configured to each receive two leads. The set screws 28 may be positioned on the side of the header 20 rather than on the top (e.g., as depicted in FIG. 4C). Thus, the set screws 28 of each of the headers 20 may be accessible from one side face of the device 10 allowing for loosening or tightening of the screws while the device is in a subcutaneous pocket of a patient.

Receptacles (not shown) of devices 10 as depicted in FIGS. 9-10 may contain redundant contacts; i.e. contacts of different receptacles coupled to the same channel of the electronics of the device, as described above. In some embodiments, receptacles in different headers 20 contain contacts coupled to the same channel of the electronics of the device.

The design of receptacles having redundant contacts as discussed above allows for a good deal of flexibility in the types of leads that a physician may choose to employ. In addition, such designs allow for manufacture of a signal generator with fewer channels than receptacle contacts, which can significantly reduce manufacturing costs and time. Of course the signal generators described herein may contain any number of channels and the receptacles may be grouped and arranged in any desirable manner provided that at least one contact of one lead is coupled to the same channel of a contact of another receptacle.

Figure 11:
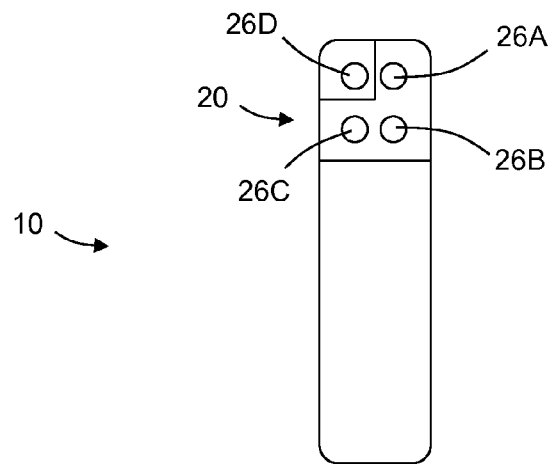
FIG. 11 is a schematic front view of an embodiment of an electrical medical device.
Figure 12:
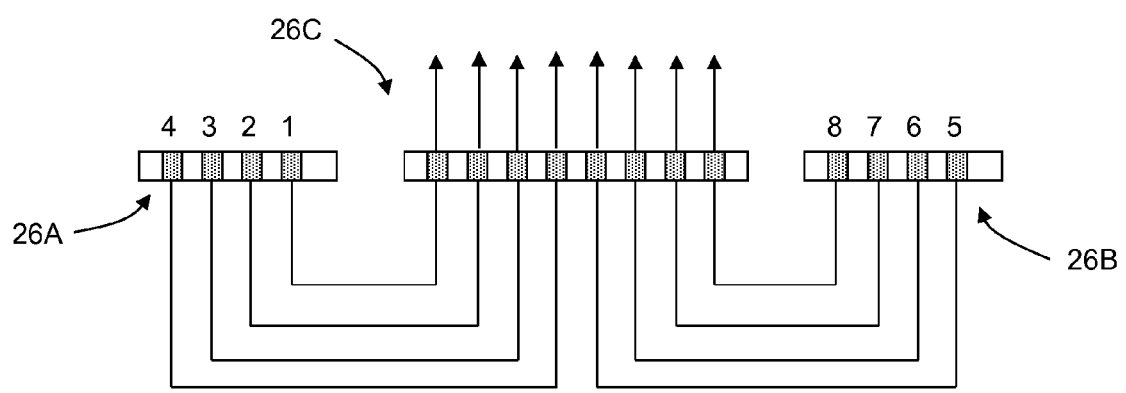
FIG. 12 is a schematic diagram showing electrical coupling of contacts of selected receptacles in an embodiment of a device depicted in FIG. 11.

An embodiment of another implantable electrical medical device 10 with redundant contacts is depicted in FIGS. 11-12. The device 10 depicted in FIG. 11 has four lead receptacles 26A, 26B, 26C, 26D. At least two of the receptacles have contacts coupled to the same channel of the electronics of the device. By using redundant channels, an increased variety of lead types may be used in configuration with one device.

By way of example, and referring to FIG. 11, the electrical device has a header 20 with four receptacles 26A, 26B, 26C, 26D. Three of the receptacles 26A, 26B, 26C have redundant contacts, while the fourth 26D has contacts that are individually electrically coupled to discrete channels of the signal generator.

As an example, the implantable electrical medical device depicted in FIG. 11 may have 16 channels. Receptacle 26D may have eight contacts that are individually coupled to eight channels (e.g., channels 9-16) of the signal generator. Receptacles 26A and 26B may each have four internal contacts, and receptacle 26C may have eight internal contacts. However, as the device has only eight remaining channels, more than one of the contacts of receptacles 26A, 26B, 26C are coupled to the same channel.

FIG. 12 depicts a possible scenario for redundant contacts in the above-described situation. As shown in FIG. 11, the four contacts of receptacle 26A and four of the eight contacts of receptacle 26C may be coupled to the first four channels of the signal generator. That is, contact 1 of receptacle 26A and contact 1 of receptacle 26C may be coupled to channel 1; contact 2 of receptacle 26A and contact 2 of receptacle 26C may be coupled to channel 2; contact 3 of receptacle 26A and contact 3 of receptacle 26C may be coupled to channel 3; and contact 4 of receptacle 26A and contact 4 of receptacle 26C may be coupled to channel 4.

As shown further shown in FIG. 11, the four contacts of receptacle 26B and four of the eight contacts of receptacle 26C may be coupled to channels 5-8 of the signal generator. That is, contact 5 of receptacle 26B and contact 5 of receptacle 26C may be coupled to channel 5; contact 6 of receptacle 26B and contact 6 of receptacle 26C may be coupled to channel 6; contact 7 of receptacle 26B and contact 7 of receptacle 26C may be coupled to channel 7; and contact 8 of receptacle 26B and contact 8 of receptacle 26C may be coupled to channel 8.

Thus, a lead having eight contacts (and eight electrodes) may be inserted into either of receptacles 26C or 26D. A lead having four contacts (and four electrodes) may be inserted into either of receptacles 26A or 26B.

Accordingly, using the above-described example, a physician may choose to use an eight electrode lead (receptacle 26D) or one or two four electrode leads (receptacles 26A, 26B) or choose to use two eight electrode leads (receptacle 26C, 26D). Of course, a physician may choose to insert an appropriate lead into each of receptacles 26A-D, but completely independent electrode control of the leads will not be achievable, the lead in receptacles 26A and 26B will share channels with receptacle 26C.

The various systems described herein may be used for any suitable purposes. Such systems may be particularly advantageous for combined spinal cord stimulation and peripheral nerve stimulation. In many cases it is desirable to use two leads, each having eight electrodes, for spinal cord stimulation. For peripheral nerve stimulation, it is often desirable to provide stimulation signals to a broader area. Thus four leads, each having four electrodes may be desired to provide broader coverage. Of course, any suitable combinations of leads and electrodes may be employed for such combined therapy.

While devices having selected numbers of receptacles, which have selected numbers of contacts, and selected numbers of channels are depicted and described herein. It will be understood that devices having any number of receptacles, such as 2, 3, 4, 5, 6, 7, 8, 9, 10 or more, which may have any number of contacts, such as 2, 4, 8, 16, 32 or the like, are contemplated herein. Further, devices having any number of electronic channels, such as 8, 16, 32, 64 or the like, which are redundantly coupled to any number of internal contacts of the receptacles are contemplated herein.

It will be understood that combinations of the various embodiments described herein, or portions or components thereof, are contemplated. It will also be understood that variations from the specific embodiments shown and described herein are contemplated. For example while the devices depicted and described herein include connector headers in which lead receptacles are formed, devices in which receptacles are formed directly in the device housing are contemplated herein.

The present disclosure describes a variety of implantable electrical medical devices. A summary of some selected aspects of such devices is provided below.

In a first aspect, an implantable electrical medical device includes: (i) electronics configured to generate or receive an electrical signal, the electronics containing a plurality of channels through which the electrical signal may be transmitted; (ii) a first lead receptacle having a defined number of internal contacts, wherein each of the internal contacts are independently operably coupled to a discrete channel of the electronics; and (iii) a second lead receptacle having a defined number of internal contacts, wherein the defined number of internal contacts of the second lead receptacle is less than the defined number of internal contacts of the first lead receptacle, and wherein each of the internal contacts of the second lead receptacle are independently operably coupled to a discrete channel of the electronics; wherein at least one of the internal contacts of the first lead receptacle and at least one of the internal contacts of the second lead receptacle are operably coupled to the same channel of the electronics.

A second aspect is a device of the first aspect, wherein a first internal contact of the first lead receptacle is operably coupled to a first channel of the electronics, wherein a second internal contact of the first lead receptacle is operably coupled to a second channel of the electronics, wherein a first internal contact of the second lead receptacle is operably coupled to the first channel of the electronics, and wherein a second internal contact of the second lead receptacle is operably coupled to the second channel of the electronics.

A third aspect is a device of the first or second aspect, wherein the second lead receptacle comprises a switch activatable by insertion of a lead into the second lead receptacle, wherein the switch is biased in an off configuration and wherein insertion of the lead into the receptacle causes the switch to close a circuit to electrically couple one or more internal contacts of the second receptacle to the discrete channels of the lead.

A fourth aspect is a device of any of aspects 1-3, wherein the first lead receptacle comprises a switch activatable by insertion of a lead into the receptacle, wherein the switch is biased in an off configuration and wherein insertion of the lead into the first lead receptacle causes the switch to close a circuit to electrically couple one or more internal contacts of the first receptacle to the discrete channels of the lead.

A fifth aspect is a device of any of aspects 1-4, wherein the electronics are configured to detect whether a lead is inserted into the first or second receptacle and to send or receive signals only to contacts of the first or second receptacle if the lead is detected. By way of example, the electronics may be configured to detect impedance indicative of a lead being inserted into a receptacle.

A sixth aspect is a device of any of aspects 1-5, further comprising: (i) a housing in which the electronics are disposed; and (ii) a connector header disposed on the housing and defining first and second bores, wherein the first lead receptacle is disposed in the first bore and wherein the second lead receptacle is disposed in the second bore.

A seventh aspect is a device of any of aspects 1-6, further comprising a third lead receptacle having a defined number of internal contacts, wherein the defined number of internal contacts of the third lead receptacle is less than the defined number of internal contacts of the first lead receptacle, wherein the defined number of internal contacts of the third lead receptacle is the same or different than the defined number of internal contacts of the second lead receptacle, and wherein each of the internal contacts of the third receptacle are independently operably coupled to a discrete channel of the electronics, and wherein at least one of the internal contacts of the first lead receptacle and at least one of the internal contacts of the third lead receptacle are operably coupled to the same channel of the electronics.

An eighth aspect is a device of the seventh aspect, wherein the sum of the defined number of internal contacts of the second lead receptacle and the defined number of internal contacts of the third lead receptacle equals the defined number of internal contacts of the first lead receptacle.

A ninth aspect is a device of the eighth aspect, wherein each of the internal contacts of the second lead receptacle is operably coupled to a channel of the electronics to which an internal contact of the first lead receptacle is operably coupled, and wherein each of the internal contacts of the third lead receptacle is operably coupled to a channel of the electronics to which an internal contact of the first lead receptacle is operably coupled.

A tenth aspect is a device of any of aspects 7-9, wherein each of the internal contacts of the second receptacle are coupled to channels different from each of the internal contacts of the third receptacle.

An eleventh aspect is an implantable medical system comprising the implantable electrical medical device of any of aspects 1-10 and one or more leads configured to be inserted into the first or second lead receptacle.

In an twelfth aspect an implantable electrical medical device includes: (i) electronics configured to generate or receive an electrical signal, the electronics containing a plurality of channels through which the electrical signal may be transmitted; (ii) a first lead receptacle having a defined number of internal contacts, wherein each of the internal contacts is independently operably coupled to a discrete channel of the electronics; (iii) a second lead receptacle having a defined number of internal contacts, wherein each of the internal contacts is independently operably coupled to a discrete channel of the electronics; and (iv) a third lead receptacle having a defined number of internal contacts, wherein each of the internal contacts is independently operably coupled to a discrete channel of the electronics; wherein a first set of one or more of the internal contacts of the first lead receptacle and a set of one or more of the internal contacts of the second lead receptacle are independently operably coupled to the same first set of one or more channels of the electronics, wherein a second set of one or more of the internal contacts of the first lead receptacle and a set of one or more of the internal contacts of the third lead receptacle are independently operably coupled to the same second set of one or more channels of the electronics, and wherein each of the contacts of the first set of internal contacts of the first lead receptacle is different from each of the contacts of the second set of internal contacts of the first lead receptacle.

A thirteenth aspect is a device of the twelfth aspect, wherein the sum of the number of contacts in the first set of internal contacts of the first lead receptacle and the number of contacts in the second set of internal contacts of the first lead receptacle equals the total number of internal contacts in the first receptacle.

A fourteenth aspect is a device of the twelfth aspect or the twelfth aspect, wherein the defined number of contacts of the second lead receptacle equals the defined number of contact of the third lead receptacle.

A fifteenth aspect is a device of any of aspects 12-14, wherein each of the contacts of the second lead receptacle is operably coupled to a channel of the electronics to which a contact of the first set of contacts of the first lead receptacle is coupled.

A sixteenth aspect is a device of any of aspects 12-15, wherein each of the contacts of the third lead receptacle is operably coupled to a channel of the electronics to which a contact of the second set of contacts of the first lead receptacle is coupled.

A seventeenth aspect is a device of any of aspects 12-16, wherein the second lead receptacle comprises a switch activatable by insertion of a lead into the second lead receptacle, wherein the switch is biased in an off configuration and wherein insertion of the lead into the second lead receptacle causes the switch to close a circuit to electrically couple one or more internal contacts of the second receptacle to the discrete channels of the electronics.

An eighteenth aspect is a device of any of aspects 12-17, wherein the third receptacle comprises a switch activatable by insertion of a lead into the receptacle, wherein the switch is biased in an off configuration and wherein insertion of the lead into the third lead receptacle causes the switch to close a circuit to electrically couple one or more internal contacts of the third lead receptacle to the discrete channels of the electronics.

A nineteenth aspect is a device of any of aspects 12-18, wherein the first lead receptacle comprises a switch activatable by insertion of a lead into the first lead receptacle, wherein the switch is biased in an off configuration and wherein insertion of the lead into the first lead receptacle causes the switch to close a circuit to electrically couple one or more internal contacts of the first lead receptacle to the discrete channels of the electronics.

A twentieth aspect is a device of any of aspects 12-19, wherein the electronics are configured to detect whether a lead is inserted into the first, second or third receptacle and to transmit signals only to or from contacts of the first, second or third lead receptacle if the lead is detected in the receptacle. By way of example, the electronics may be configured to detect impedance indicative of a lead being inserted into a receptacle.

A twenty-first aspect is a device of any and of aspects 12-20, wherein the second and third lead receptacles are configured to receive leads having the same number of contacts, but with different spacing of the contacts on the leads.

A twenty-second aspect is a system comprising an implantable electrical medical device of any of aspects 12-21 and one or more leads configured to be inserted into the first, second, or third lead receptacle.

In a twenty-third aspect, an implantable electrical medical device comprises (i) electronics configured to generate or receive an electrical signal, the electronics containing a plurality of channels through which the electrical signal may be transmitted; (ii) a first lead receptacle having a defined number of internal contacts, wherein each of the internal contacts are independently operably coupled to a discrete channel of the electronics; and (iii) a second lead receptacle having the same number of internal contacts as the first lead receptacle, and wherein each of the internal contacts of the second receptacle are independently operably coupled to a discrete channel of the electronics, wherein each channel of the electronics to which a contact of the first receptacle is operably coupled is also operably coupled to a channel of the second receptacle, and wherein the first and second lead receptacle are configured to receive leads having contacts with different spacing.

A twenty-fourth aspect is an implantable medical system comprising the implantable electrical medical device of the twenty-third aspect and one or more leads configured to be inserted into the first or second lead receptacle.

In a twenty-fifth aspect, a method for manufacturing an implantable medical device having redundant connections between contacts of one or more lead receptacles and channels of electronics includes (i) providing a device body having a hermetically sealed housing, electronics disposed in the housing, and a plurality of feedthroughs extending through the hermetically sealed housing, wherein each of the plurality of feedthroughs is electrically coupled to a discrete channel of the electronics; (ii) providing a header having first and second lead receptacles into which leads may be inserted, the first and second lead receptacle each having a defined number of internal contacts wherein the defined number of internal contacts of the second lead receptacle is less than the defined number of internal contacts of the first lead receptacle; (iii) electrically coupling each of the contacts of the first lead receptacle to a discrete channel of the electronics; and (iv) electrically coupling each of the contacts of the second lead receptacle to a discrete channel of the electronics, wherein at least one of the internal contacts of the first lead receptacle and at least one of the internal contacts of the second lead receptacle are operably coupled to the same channel of the electronics.

In a twenty-sixth aspect, a method for manufacturing an implantable medical device having redundant connections between contacts of one or more lead receptacles and channels of electronics includes (i) providing a device body having a hermetically sealed housing, electronics disposed in the housing, and a plurality of feedthroughs extending through the hermetically sealed housing, wherein each of the plurality of feedthroughs is electrically coupled to a discrete channel of the electronics; (ii) providing a header having first, second and third lead receptacles into which leads may be inserted, the first and second lead receptacle each having a defined number of internal contacts wherein the defined number of internal contacts of the second lead receptacle is less than the defined number of internal contacts of the first lead receptacle; (iii) electrically coupling each of the contacts of the first lead receptacle to a discrete channel of the electronics; (iv) electrically coupling each of the contacts of the second lead receptacle to a discrete channel of the electronics; and (v) electrically coupling each of the contacts of the third lead receptacle to a discrete channel of the electronics, wherein a first set of one or more of the internal contacts of the first lead receptacle and a set of one or more of the internal contacts of the second lead receptacle are independently operably coupled to the same first set of one or more channels of the electronics, wherein a second set of one or more of the internal contacts of the first lead receptacle and a set of one or more of the internal contacts of the third lead receptacle are independently operably coupled to the same second set of one or more channels of the electronics, and wherein each of the contacts of the first set of internal contacts of the first lead receptacle is different from each of the contacts of the second set of internal contacts of the first lead receptacle.

In a twenty-seventh aspect, a method for manufacturing an implantable medical device having redundant connections between contacts of one or more lead receptacles and channels of electronics includes (i) providing a device body having a hermetically sealed housing, electronics disposed in the housing, and a plurality of feedthroughs extending through the hermetically sealed housing, wherein each of the plurality of feedthroughs is electrically coupled to a discrete channel of the electronics; (ii) providing a header having first and second lead receptacles into which leads may be inserted, the first and second lead receptacle each having a defined number of internal contacts wherein the defined number of internal contacts of the second lead receptacle is less than the defined number of internal contacts of the first lead receptacle; (iii) electrically coupling each of the contacts of the first lead receptacle to a discrete channel of the electronics; and (iv) electrically coupling each of the contacts of the second lead receptacle to a discrete channel of the electronics, wherein each channel of the electronics to which a contact of the first receptacle is operably coupled is also operably coupled to a channel of the second receptacle, and wherein the first and second lead receptacle are configured to receive leads having contacts with different spacing.

Thus, embodiments of the VARYING LEAD CONFIGURATION IMPLANTABLE MEDICAL DEVICE are disclosed. One skilled in the art will appreciate that the present invention can be practiced with embodiments other than those disclosed. The disclosed embodiments are presented for purposes of illustration and not limitation.

What is claimed is:

1. An implantable electrical medical device comprising:
   electronics configured to generate or receive an electrical signal, the electronics containing a plurality of channels through which the electrical signal may be transmitted;
   a first lead receptacle having a defined number of internal contacts, wherein each of the internal contacts are independently operably coupled to a discrete channel of the electronics; and
   a second lead receptacle having a defined number of internal contacts, wherein the defined number of internal contacts of the second lead receptacle is less than the defined number of internal contacts of the first lead receptacle, and wherein each of the internal contacts of the second lead receptacle are independently operably coupled to a discrete channel of the electronics;
   wherein at least one of the internal contacts of the first lead receptacle and at least one of the internal contacts of the second lead receptacle are operably coupled to the same channel of the electronics.

2. The implantable electrical medical device of claim 1, wherein a first internal contact of the first lead receptacle is operably coupled to a first channel of the electronics, wherein a second internal contact of the first lead receptacle is operably coupled to a second channel of the electronics, wherein a first internal contact of the second lead receptacle is operably coupled to the first channel of the electronics, and wherein a second internal contact of the second lead receptacle is operably coupled to the second channel of the electronics.

3. The implantable electrical medical device of claim 1, wherein the second receptacle comprises a switch activatable by insertion of a lead into the second receptacle, wherein the switch is biased in an off configuration and wherein insertion of the lead into the second receptacle causes the switch to close a circuit to electrically couple one or more internal contacts of the second receptacle to the discrete channels of the lead.

4. The implantable electrical medical device of claim 1, wherein the first lead receptacle comprises a switch activatable by insertion of a lead into the first lead receptacle, wherein the switch is biased in an off configuration and wherein insertion of the lead into the first lead receptacle causes the switch to close a circuit to electrically couple one or more internal contacts of the first lead receptacle to the discrete channels of the lead.

5. The implantable electrical medical device of claim 1, wherein the electronics are configured to detect whether a lead is inserted into the first or second receptacle and to send or receive signals only to contacts of the first or second receptacle if the lead is detected.

6. The implantable medical device of claim 1, further comprising:
   a housing in which the electronics are disposed;
   a connector header disposed on the housing and defining first and second bores, wherein the first lead receptacle is disposed in the first bore and wherein the second lead receptacle is disposed in the second bore.

7. The implantable electrical medical device of claim 1, further comprising:
   a third lead receptacle having a defined number of internal contacts, wherein the defined number of internal contacts of the third lead receptacle is less than the defined number of internal contacts of the first lead receptacle, wherein the defined number of internal contacts of the third lead receptacle is the same or different than the defined number of internal contacts of the second lead receptacle, and wherein each of the internal contacts of the third receptacle are independently operably coupled to a discrete channel of the electronics, and
   wherein at least one of the internal contacts of the first lead receptacle and at least one of the internal contacts of the third lead receptacle are operably coupled to the same channel of the electronics.

8. The implantable electrical medical device of claim 7, wherein the sum of the defined number of internal contacts of the second lead receptacle and the defined number of internal contacts of the third lead receptacle equals the defined number of internal contacts of the first lead receptacle.

9. The implantable medical device of claim 8, wherein each of the internal contacts of the second lead receptacle is operably coupled to a channel of the electronics to which an internal contact of the first lead receptacle is operably coupled, and
   wherein each of the internal contacts of the third lead receptacle is operably coupled to a channel of the electronics to which an internal contact of the first lead receptacle is operably coupled.

10. The implantable medical device of claim 7, wherein each of the internal contacts of the second lead receptacle are coupled to channels different from each of the internal contacts of the third lead receptacle.

11. The implantable electrical medical device of claim 1, further comprising:
    a third lead receptacle having a defined number of internal contacts, wherein each of the internal contacts is independently operably coupled to a discrete channel of the electronics;
    wherein a first set of one or more of the internal contacts of the first lead receptacle comprises at least one of the internal contacts of the first lead receptacle that is operably coupled to the same channel of the electronics as the at least one internal contacts of the second lead receptacle,
    wherein a set of one or more of the internal contacts of the second lead receptacle comprises the at least one of the internal contacts of the second lead receptacle that is operably coupled to the same channel of the electronics as the at least one internal contacts of the first lead receptacle, wherein the first set of one or more of the internal contacts of the first lead receptacle and the set of one or more of the internal contacts of the second lead receptacle are independently operably coupled to a same first set of one or more channels of the electronics, wherein a second set of one or more of the internal contacts of the first lead receptacle and a set of one or more of the internal contacts of the third lead receptacle are independently operably coupled to a same second set of one or more channels of the electronics, and wherein each of the contacts of the first set of internal contacts of the first lead receptacle is different from each of the contacts of the second set of internal contacts of the first lead receptacle.

12. The implantable electrical medical device of claim 11, wherein the sum of the number of contacts in the first set of internal contacts of the first lead receptacle and the number of contacts in the second set of internal contacts of the first lead receptacle equals the total number of internal contacts in the first receptacle.

13. The implantable electrical medical device of claim 11, wherein the defined number of contacts of the second lead receptacle equals the defined number of contact of the third lead receptacle.

14. The implantable electrical medical device of claim 11, wherein each of the contacts of the second lead receptacle is operably coupled to a channel of the electronics to which a contact of the first set of contacts of the first lead receptacle is coupled.

15. The implantable electrical medical device of claim 11, wherein each of the contacts of the third lead receptacle is operably coupled to a channel of the electronics to which a contact of the second set of contacts of the first lead receptacle is coupled.

16. The implantable electrical medical device of claim 11, wherein the second lead receptacle comprises a switch activatable by insertion of a lead into the receptacle, wherein the switch is biased in an off configuration and wherein insertion of the lead into the second lead receptacle causes the switch to close a circuit to electrically couple one or more internal contacts of the second lead receptacle to discrete channels of the electronics.

17. The implantable electrical medical device of claim 11, wherein the third lead receptacle comprises a switch activatable by insertion of a lead into the receptacle, wherein the switch is biased in an off configuration and wherein insertion of the lead into the third lead receptacle causes the switch to close a circuit to electrically couple one or more internal contacts of the third receptacle to discrete channels of the electronics.

18. The implantable electrical medical device of claim 11, wherein the first lead receptacle comprises a switch activatable by insertion of a lead into the receptacle, wherein the switch is biased in an off configuration and wherein insertion of the lead into the first lead receptacle causes the switch to close a circuit to electrically couple one or more internal contacts of the first receptacle to discrete channels of the electronics.

19. The implantable electrical medical device of claim 11, wherein the electronics are configured to detect whether a lead is inserted into the first, second or third receptacle and to transmit signals only to or from contacts of the first, second or third lead receptacles if the lead is detected in the receptacle.

20. An implantable electrical medical device of claim 11, wherein the second and third lead receptacles are configured to receive leads having the same number of contacts, but with different spacing of the contacts on the leads.

* * * * *